United States Patent [19]
Thym et al.

[11] 4,179,465
[45] Dec. 18, 1979

[54] N-FLUOROMETHYL-CARBAMIC ACID FLUORIDES AND THEIR MANUFACTURE

[75] Inventors: Sabine Thym, Heidelberg-Dossenheim; Karl-Heinz Koenig, Frankenthal; Gerhard Hamprecht, Mannheim, all of Fed. Rep. of Germany

[73] Assignee: BASF Aktiengesellschaft, Fed. Rep. of Germany

[21] Appl. No.: 869,383

[22] Filed: Jan. 13, 1978

[30] Foreign Application Priority Data

Feb. 17, 1977 [DE] Fed. Rep. of Germany ....... 2706683

[51] Int. Cl.$^2$ ..................... C07C 51/58; C07C 125/00
[52] U.S. Cl. ................................................ 260/544 C
[58] Field of Search ..................................... 260/544 C

[56] References Cited
PUBLICATIONS

Weygand, "Preparative Organic Chemistry" pp. 204–209 (1973).

*Primary Examiner*—Gerald A. Schwartz
*Attorney, Agent, or Firm*—Keil & Witherspoon

[57] ABSTRACT

New N-fluoromethyl-carbamic acid fluorides and a new process for their manufacture by reacting N-halomethyl-carbamic acid halides with metal fluorides. The products are starting materials for the manufacture of drugs, dyes, pesticides, plastics, plastics auxiliaries and textile auxiliaries.

5 Claims, No Drawings

N-FLUOROMETHYL-CARBAMIC ACID FLUORIDES AND THEIR MANUFACTURE

The present invention relates to new N-fluoromethyl-carbamic acid fluorides and a new process for their manufacture by reacting N-halomethyl-carbamic acid halides with metal fluorides.

Houben-Weyl, Methoden der Organischen Chemie, Volume V/3, page 148 discloses that the reaction of carboxylic acid chlorides with potassium fluoride to give carboxylic acid fluorides is substantially more difficult than the reaction of sulfochlorides with potassium fluoride to give sulfofluorides; glacial acetic acid and acetic anhydride are recommended as the reaction medium for achieving a satisfactory yield. If a halocarboxylic acid chloride is heated with potassium hydrogen fluoride on a waterbath (Houben-Weyl, loc. cit., pages 149 and 150), the corresponding halocarboxylic acid fluoride is obtained. The halogen present as an α-substituent in the carboxylic acid is not split off during the reaction, so that, for example, chloroacetyl fluoride, dichloroacetyl fluoride, trichloroacetyl fluoride, bromoacetyl fluoride or iodoacetyl fluoride is formed from the corresponding chloride.

The manufacture of N-fluoromethyl-carbamic acid fluorides has not previously been disclosed.

α-Haloalkyl-carbamic acid halides are at one and the same time acid halides and α-Haloalkylamines, i.e. they contain two reactive centers. α-haloalkylamines are very reactive compounds, and acid halides are also known to be extremely reactive. It could therefore not be foreseen which of the two reactive halogen atoms would react with a metal fluoride, and to what degree.

We have found that an N-fluoromethyl-carbamic acid fluoride of the formula

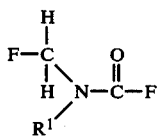

where R¹ is a cycloaliphatic radical or is

R², R³ and R⁴ may be identical or different and each is hydrogen or an aliphatic radical, and in addition R² may be fluorine if R³ and R⁴ are each hydrogen is obtained in an advantageous manner if a halomethyl-carbamic acid halide of the formula

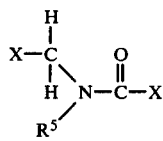

where the individual radicals X are each chlorine or bromine and R⁵ has the same meaning as R¹ or, if R² is fluorine, may also represent

where X has the above meaning, is reacted with a fluoride of a metal of group Ia, Ib, IIa, IIb, IIIa, IIIb, IVa, IVb, Va, VIb, VIIb or VIIIb of the periodic table.

Further, we have found the new N-fluoromethyl-carbamic acid fluorides of the formula

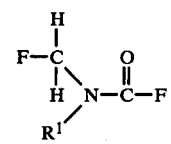

where R¹ is a cycloaliphatic radical or is

R², R³ and R⁴ may be identical or different and each is hydrogen or an aliphatic radical, in addition R² may be fluorine if R³ and R⁴ are each hydrogen.

Where N-chloromethyl-N-methyl-carbamic acid chloride and potassium fluoride are used, the reaction may be represented by the following equation:

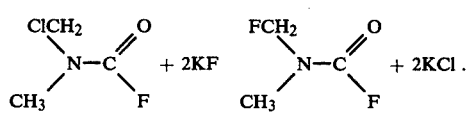

The process of the invention is surprising in view of the prior art and gives N-fluoromethyl-carbamic acid fluorides in a simple and economical manner, in good yield and high purity. In view of the conventional processes, it was not to be expected that fluorine would replace the original halogen substituted both on the α-carbon atom and on the acid halide group. Equally, increased formation of byproducts and decomposition products might have been expected in view of the reactivity of both the fluorine and the carbamido group. It is therefore surprising that a high yield of a pure, single end product is obtained in place of the heterogeneous mixture of numerous components which might have been expected.

The starting materials II can easily be manufactured, for example by the processes disclosed in German Published Application DAS 1,154,087 (reaction of a carbamic acid chloride or carbamic acid bromide with bromine or chlorine), German Published Application DAS 1,153,756 (reaction of 1,3,5-trialkylhexahydro-s-triazines with haloacyl compounds) and German Laid-Open Appliction DOS 2,043,235 (reaction of a Schiff base with phosgene). Preferred starting materials II and accordingly preferred end products I are those where R¹ is cycloalkyl of 5 to 8 carbon atoms or is

$R^2$, $R^3$ and $R^4$ may be identical or different and each is hydrogen or alkyl of 1 to 20, especially of 1 to 7, carbon atoms or alkenyl of 2 to 20, especially of 2 to 7, carbon atoms, in addition $R^2$ may also be fluorine if $R^3$ and $R^4$ are each hydrogen, the individual radicals X are different or, preferably, identical, and each is chlorine or bromine and $R^5$ has the meaning of $R^1$ or, if $R^2$ is fluorine, may also be

where X has the above meaning. The above radicals may in addition be substituted by groups which are inert under the reaction conditions, e.g. alkyl of 1 to 4 carbon atoms.

Examples of suitable starting materials II are N-methyl-, N-ethyl-, N-n-propyl-, N-isopropyl-, N-n-butyl-, N-isobutyl-, N-sec.-butyl-, N-tert.-butyl-, N-pentyl-, N-isopentyl-, N-hexyl-, N-heptyl-, N-octyl-, N-isooctyl-, N-allyl-, N-crotyl-, N-undec-11-en-1-yl-, N-oleyl-, N-cyclopentyl-, N-cyclohexyl-, N-cycloheptyl-, N-cycloocytyl-, N-fluoromethyl- and N-bromomethyl-N-chloromethyl-carbamic acid chloride, N,N-bis-(chloromethyl)-carbamic acid chloride and the corresponding N-bromomethyl-carbamic acid bromides; preferred starting materials are N-chloromethyl-N-methyl-carbamic acid chloride, N,N-bis-(chloromethyl)-carbamic acid chloride, N-chloromethyl-N-isopropyl-carbamic acid chloride, N-chloromethyl-N-tert.-butyl-carbamic acid chloride and N-chloromethyl-N-cyclohexyl-carbamic acid chloride.

The other starting materials used are metal fluorides of metals of groups Ia, Ib, IIa, IIb, IIIa, IIIb, IVa, IVb, Va, VIb, VIIb and VIIIb, preferably of groups Ia, IIa, IIIa, IVa, Va and IIb, of the periodic table. The groups mentioned are as defined in D'Ans-Lax, Taschenbuch für Chemiker und Physiker (Springer, Berlin, 1967), Volume 1, page 63 (corresponding to Weast, Handbook of Chemistry and Physics (The Chemical Rubber Co., Cleveland, 50th ed.), page B 3, and Clark, The Encyclopaedia of Chemistry, 2nd edition (Reinhold Pub. Corp., N.Y., 1966), page 790). Advantageous fluorides to use are sodium fluoride, potassium fluoride, potassium hydrogen fluoride, sodium hydrogen fluoride, lithium fluoride, calcium fluoride, barium fluoride, magnesium fluoride, silver(I) fluoride, silver(II) fluoride, zinc(II) fluoride, mercury(I) fluoride, mercury(II) fluoride, cadmium(II) fluoride, beryllium(II) fluoride, copper(II) fluoride, boron(III) fluoride, aluminum(III) fluoride, cerium(III) fluoride, thallium(I) fluoride, zirconium-(IV) fluoride, titanium(III) fluoride, titanium(IV) fluoride, tin(II) fluoride, tin(IV) fluoride, lead(II) fluoride, lead(IV) fluoride, arsenic(III) fluoride, arsenic(V) fluoride, antimony(III) fluoride, antimony(V) fluoride, bismuth(V) fluoride, molybdenum(III) fluoride, molybdenum(IV) fluoride, uranium(IV) fluoride, uranium(VI) fluoride, manganese(II) fluoride, manganese(III) fluoride, iron(II) fluoride, iron(III) fluoride, cobalt(II) fluoride and cobalt(III) fluoride. KF, $KHF_2$, $CaF_2$, NaF, $NaHF_2$, $MgF_2$, and $SbF_3$ are preferred. The metal fluoride may be used in the stoichiometric amount or in excess, advantageously in an amount of from 1 to 3 equivalents of metal fluoride per halogen atom of the carbamic acid halide group and of the α-carbon atoms of starting material II. Accordingly, the stoichiometric requirement is 2 equivalents of fluoride, e.g. 2 moles of KF or 1 mole of $CaF_2$, per mole of monohalomethylcarbamic acid halide, and 3 equivalents of fluoride, e.g. 1 mole of $AlF_3$ or 1.5 moles of $CaF_2$, per mole of dihalomethyl compound II.

The reaction is as a rule carried out at from 40° to 300° C., preferably from 60° to 200° C., especially from 95° to 162° C., under atmospheric or superatmospheric pressure, continuously or batchwise. It is advantageous to use organic solvents which are inert under the reaction conditions, examples being ethers, e.g. ethyl propyl ether, methyl tert.-butyl ether, N-butyl ethyl ether, di-n-butyl ether, diisobutyl ether, diisoamyl ether, diisopropyl ether, anisole, phenetole, cyclohexyl methyl ether, diethyl ether, tetrahydrofuran, dioxane, thioanisole and β,β'-dichlorodiethyl ether, polyethylene glycol ethers, e.g. ethylene glycol dimethyl ether, diethyl ether, di-n-propyl ether, diisopropyl ether, di-n-butyl ether, diisobutyl ether, di-sec.-butyl ether and di-tert.-butyl ether, diethylene glycol dimethyl ether, diethyl ether, di-n-propyl ether, diisopropyl ether, di-n-butyl ether, diisobutyl ether, di-sec.-butyl ether and di-tert.-butyl ether, and corresponding diethers of triethylene glycol and of tetraethylene glycol, sulfoxides, e.g. dimethylsulfoxide and diethylsulfoxide, dimethyl sulfone, diethyl sulfone, methyl ethyl sulfone and tetramethylene sulfone (sulfolan), N-methylpyrrolidone, dimethylformamide, hexamethylphosphorotriamide and mixtures of these. Advantageously, the solvent is used in an amount of from 400 to 10,000 percent by weight, preferably from 500 to 2,000 percent by weight, based on starting material II.

The reaction may be carried out as follows: a mixture of the starting material II, a metal fluoride and, advantageously, a solvent is kept at the reaction temperature for from ½ to 10 hours. In one embodiment, the process may be carried out by adding the carbamic acid halide reactant, which may or may not be dissolved in a solvent, to a solution or suspension containing the metal fluoride and heating the mixture to the reaction temperature. However, it is more advantageous to heat the metal fluoride solution or suspension to the reaction temperature and add the carbamic acid halide slowly so as to keep the temperature constant. The end product is then isolated from the reaction mixture in the conventional manner, e.g. by fractional distillation.

The new compounds which may be manufactured by the process of the invention are valuable starting materials for the manufacture of drugs, dyes, pesticides, plastics, plastics auxiliaries and textile auxiliaries. For example, reaction of the end products I with phenols or amines gives, respectively, the corresponding carbamates or ureas, which are valuable active ingredients of, for example, herbicides and fungicides (Examples 6 to 8). Reaction of the end products I with alkenols gives valuable starting materials for the manufacture of coating intermediates, plastics, paints and crop protection agents. The products can be copolymerized with other monomers, e.g. acrylic acid esters, methacrylic acid esters and styrene. Regarding the copolymerization, reference may be made to Houben-Weyl, Methoden der Organischen Chemie, Volume 14/1, page 24 (1961). The copolymers may be used with advantage as coatings or films on building materials, e.g. on wood, stone or concrete surfaces. Such coatings or films can be produced by any desired conventional method (Ullmanns Encyclopädie der technischen Chemie, Volume 11, pages 283 and 367 et seq. (1960)). Equally, the products obtained from alkenols and the compounds I can be used to produce, by polymerization, advantageous crosslinking agents for polyamines. The polyamines are crosslinked by, for example, the processes described in Houben-Weyl, loc. cit. The products obtained by reacting the compounds I with alcohols and/or water can be reacted with diamines or polyamines to give urea compounds which are valuable antistatic agents. Reaction of the end products I with tribromoaniline gives urea derivatives with flameproofing properties. For the above uses, it is advantageous to employ the preferred end products, in particular N-fluoromethyl-N-methyl-carbamic acid fluoride, N,N-bis-(fluoromethyl)-carbamic acid fluoride, N-fluoromethyl-N-isopropyl-carbamic acid fluoride, N-fluoromethyl-N-tert.-butyl-carbamic acid fluoride and N-fluoromethyl-N-cyclohexyl-carbamic acid fluoride.

In the Examples which follow, parts are by weight, and bear the same relation to parts by volume as that of the kilogram to the liter.

EXAMPLE 1

139 parts of potassium fluoride are suspended in 300 parts by volume of sulfolan and heated to 160° C., with vigorous stirring. At this temperature, 85 parts of N-chloromethyl-N-methyl-carbamic acid chloride are added whilst keeping the temperature constant. The mixture is then stirred for a further 2 hours at 160° C., after which it is distilled. 45 parts (69% of theory) of N-fluoromethyl-N-methyl-carbamic acid fluoride of boiling point 37°–38° C./27 mm Hg and refractive index $n_D^{25} = 1.375$ are obtained.

EXAMPLE 2

348 parts of potassium fluoride are suspended in 500 parts by volume of sulfolan and the mixture is heated to 140° C. 160 parts of N,N-bis-(chloromethyl)-carbamic acid chloride are added at from 130° to 140° C. whilst keeping the temperature constant. The mixture is then left at from 130° to 140° C. for a further 3 hours. After fractional distillation under reduced pressure, 57 parts (50% of theory) of N,N-bis-(fluoromethyl)-carbamic acid fluoride of boiling point 56° C./35 mm Hg and refractive index $n_D^{20} = 1.366$ are obtained.

EXAMPLE 3

174 parts of potassium fluoride are suspended in 200 parts by volume of sulfolan and the suspension is heated to 120° C., at which temperature 166 parts of N-tert.-butyl-N-chloromethyl-carbamic acid chloride are added. The mixture is stirred for a further 2 hours at 120° C. and then distilled. 93 parts (68% of theory) of N-tert.-butyl-N-fluoromethyl-carbamic acid fluoride of refractive index $n_D^{23} = 1.398$ and boiling point 90° C./77 mm Hg are obtained.

EXAMPLE 4

743 parts of potassium fluoride in 800 parts by volume of sulfolan are heated to 100° C., and at this temperature 530 parts of N-chloromethyl-N-isopropyl-carbamic acid chloride are added. After 2.5 hours, the mixture is distilled. 295 parts (69% of theory) of N-fluoromethyl-N-isopropyl-carbamic acid fluoride of refractive index $n_D^{21} = 1.389$ and boiling point 50° C./13 mm Hg are obtained.

EXAMPLE 5

188 parts of potassium fluoride in 200 parts by volume of sulfolan are heated to 100° C. and whilst keeping this temperature constant, 170 parts of N-chloromethyl-N-cyclohexyl-carbamic acid chloride are added. The mixture is stirred for a further 2.5 hours at 100° C. and is then distilled under reduced pressure. 81 parts (57% of theory) of N-fluoromethyl-N-cyclohexyl-carbamic acid fluoride of refractive index $n_D^{22} = 1.441$ and boiling point 45° C./0.01 mm Hg are obtained.

EXAMPLE 6 (USE)

(a) O-3-Isopropyl-5-methyl-phenyl N,N-bis-fluoromethyl-carbamate 16 parts of 80 percent strength by weight 3-isopropyl-5-methyl-phenol in 30 parts of methylene chloride are added to 12.7 parts of N,N-bis-fluoromethyl-carbamic acid fluoride (from Example 2) in 50 parts of methylene chloride. 10.1 parts of triethylamine in 20 parts of methylene chloride are then added. The reaction mixture is stirred for one hour at 40° C. and when it has cooled it is extracted by shaking with 10 percent strength by weight sodium hydroxide solution and water, dried and distilled to dryness under reduced pressure. 24.1 parts (95% of theory) of O-3-isopropyl-5-methyl-phenyl N,N-bis-fluoromethyl-carbamate of boiling point 120° C./0.05 mm Hg are obtained.

(b) 5 ml of double-strength nutrient broth are added to 5 ml of an 0.2 percent strength solution of O-3-isopropyl-5-methylphenyl N,N-bis-fluoromethyl-carbamate in water, in a sterile test tube, and the components are mixed. The contents of the test tube are then inoculated with one drop of a 16 hours' old Staphylococcus aureus culture which has been diluted 1:10, and are incubated for 72 hours at 37° C. After this time, samples are transferred from the test tube to nutrient media for bacteria and these are incubated for 24 hours at 37° C. The nutrient media treated with the samples contain 100 ppm of active ingredient in suspension. After transfer to the nutrient media for bacteria, no bacterial growth is detectable in the samples containing the above active ingredient, in contrast to the controls to which the active ingredient has not been added.

EXAMPLE 7 (USE)

(a) O-3,5-Dichloro-phenyl N,N-bis-fluoromethyl-carbamate 16.3 parts of 3,5-dichlorophenol and 15.3 parts of N,N-dimethylcyclohexylamine are introduced into 100 parts of toluene. 12.7 parts of N,N-bis-fluoromethyl-carbamic acid fluoride (from Example 2) are added in portions at from 10° to 22° C., with thorough mixing. The batch is then stirred for 20 minutes at 70° C. When it has cooled, the mixture is extracted by shaking with 10 percent strength by weight sodium hydroxide solution and with water, and is dried, and distilled to dryness under reduced pressure. 25.8 parts of O-3,5-dichlorophenyl N,N-bis-fluoromethyl-carbamate (70% of theory), having a melting point of 76°–78° C. after recrystallization from cyclohexane, are obtained. (b) 5 ml of double-strength nutrient broth are added to 5 ml portions of an 0.2 percent strength solution of the end product from Example 7(a) in water, in a sterile test tube, and the components are mixed. The contents of the test tube are then inoculated with one drop of a 16 hours' old Staphylococcus aureus culture which has been diluted 1:10, and are incubated for 72 hours at 37° C. After this time, samples are transferred from the test tube to nutrient media for bacteria and these are incubated for 24 hours at 37° C. The nutrient media treated with the samples contain 100 ppm of active ingredient in suspension. After transfer to the nutrient media for bacteria, no bacterial growth is detectable in the samples containing the above active ingredient, in contrast to the controls to which the active ingredient has not been added.

EXAMPLE 8 (USE)

(a) N,N-Bis-fluoromethyl-N'-methyl-N'-(2-benzthiazolyl)-urea 4 parts of a mixture of 80 parts of sodium hydride and 20 parts of white oil are introduced into 50 parts of tetrahydrofuran. 21.4 parts of 2-(methylamino)-benthiazole in 250 parts of tetrahydrofuran are added in portions at from 25° to 35° C. The reaction mixture is stirred for 2 hours at 40° C. and 17 parts of N,N-bis-fluoromethylcarbamic acid fluoride (from Example 2) are then added at 22° C. After 4 hours, the mixture is filtered, the filtrate is concentrated under reduced pressure and the residue is stirred with ethyl acetate. 1.5 parts of N,N-bis-fluoromethyl-N'-methyl-N'-(2-benzthiazolyl)-urea of melting point 131°–134° C. are obtained. (b) The end product from Example 8(a) is tested for its herbicidal and fungicidal properties. It possesses a good herbicidal action which manifests itself particularly when used in connection with crops; the latter are not damaged.

We claim:

1. A process for the manufacture of a N-fluoromethyl-carbamic acid fluoride of the formula

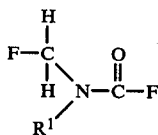
I where R¹ is a cycloaliphatic radical or is

where R², R³ and R⁴ may be identical or different and each is hydrogen or an aliphatic radical, and in addition R² may be fluorine if R³ and R⁴ are each hydrogen, wherein a halomethyl-carbamic acid halide of the formula

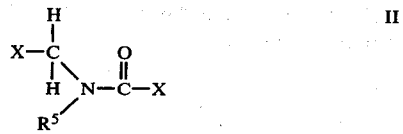
II where the individual radicals X are each chlorine or bromine and R⁵ has the same meaning as R¹ or, if R² is fluorine, may also represent

where X has the above meaning, is reacted at from 40° to 300° C. with a fluoride of a metal of groups Ia, Ib, IIa, IIb, IIIa, IIIb, IVa, IVb, Va, VIb, VIIb and VIIIb of the periodic table.

2. The process of claim 1, wherein the reaction is carried out with sodium fluoride, potassium fluoride, potassium hydrogen fluoride, sodium hydrogen fluoride, lithium fluoride, calcium fluoride, barium fluoride, magnesium fluoride, silver(I) fluoride, silver(II) fluoride, zinc(II) fluoride, mercury(I) fluoride, mercury(II) fluoride, cadmium(II) fluoride, beryllium(II) fluoride, copper(II) fluoride, boron(III) fluoride, aluminum(III) fluoride, cerium(III) fluoride, thallium(I) fluoride, zirconium(IV) fluoride, titanium(III) fluoride, titanium(IV) fluoride, tin(II) fluoride, tin(IV) fluoride, lead(II) fluoride, lead(IV) fluoride, arsenic(III) fluoride, arsenic(V) fluoride, antimony(III) fluoride, antimony(V) fluoride, bismuth(V) fluoride, molybdenum(III) fluoride, molybdenum (IV) fluoride, uranium(IV) fluoride, uranium(VI) fluoride, manganese (II) fluoride, manganese(III) fluoride, iron(II) fluoride, iron(III) fluoride, cobalt(II) fluoride and/or cobalt(III) fluoride.

3. The process of claim 1, wherein the reaction is carried out with from 1 to 3 equivalents of metal fluoride per halogen atom of the carbamic acid halide group and of the α-carbon atoms of the starting material II.

4. The process of claim 1, wherein the reaction is carried out at from 60° to 200° C.

5. The process of claim 1, wherein the reaction is carried out with from 400 to 10,000 percent by weight, based on starting material II, of an organic solvent which is inert under the reaction conditions.

* * * * *